United States Patent [19]
Fukunaga et al.

[11] Patent Number: 6,096,936
[45] Date of Patent: Aug. 1, 2000

[54] L-TYPE ZEOLITE CATALYST

[75] Inventors: Tetsuya Fukunaga; Michio Sugimoto, both of Chiba-ken, Japan; Robert A. Innes, Marin, Calif.

[73] Assignees: Idemitsu Kosan Co., Ltd., Tokyo, Japan; Chevron Chemical Company LLC, San Ramon, Calif.

[21] Appl. No.: 09/134,164

[22] Filed: Aug. 14, 1998

[51] Int. Cl.[7] ...................................................... C07C 2/52
[52] U.S. Cl. ........................... 585/419; 585/407; 585/418; 502/74
[58] Field of Search ................................ 502/64, 66, 74; 585/407, 418, 419

[56] References Cited

U.S. PATENT DOCUMENTS 4,914,068  4/1990  Cross et al. ................................. 502/74

*Primary Examiner*—Tom Dunn
*Attorney, Agent, or Firm*—Oblon, Spivak, McClelland, Maier & Neustadt, P.C.

[57] ABSTRACT

There are herein disclosed an L-type zeolite catalyst which is obtainable by supporting a platinum component, one or more halogen components and one or more metal components selected from the group Ib of the periodic table on an L-type zeolite, the support amount of one or more metal components selected from the group Ib being in the range of 0.001 to 3% by weight based on the total weight of the catalyst in terms of the metal, a molar ratio of one or more metal components selected from the group Ib/platinum being in the range of 0.01 to 1; and a method for producing aromatic hydrocarbons or a gasoline having a high octane number which comprises the step of bringing one or more fractions selected from a C6 fraction, a C7 fraction, and a C8[+] fraction into contact with this catalyst. According to the present invention, there are provided a catalyst containing an L-type zeolite as a carrier which is desirable as a catalyst for the production of aromatic hydrocarbons or a gasoline having a high octane number and which can inhibit a cracking activity and the formation of coke and can improve an aromatic selectivity and a liquid yield.

13 Claims, No Drawings

6,096,936

L-TYPE ZEOLITE CATALYST

BACKGROUND OF THE INVENTION (i) Field of the Invention

The present invention relates to an L-type catalyst containing a platinum component, one or more halogen components and one or more metals selected from the group Ib of the periodic table, a method for preparing this catalyst, and a method for producing aromatic hydrocarbons and a gasoline having a high octane number by the use of the catalyst. More specifically, the present invention relates to a catalyst suitable for the production of aromatic hydrocarbons and a gasoline having a high octane number, a method for preparing the catalyst, and a method for efficiently producing aromatic hydrocarbons and a gasoline having a high octane number by the use of the catalyst. The employment of this catalyst can restrain a cracking activity and the formation of coke, and can also improve an aromatic selectivity and a liquid yield.

(ii) Description of the Related Art

Heretofore, as catalysts for aromatizing non-aromatic hydrocarbons such as aliphatic hydrocarbons to produce aromatic hydrocarbons, platinum-aluminum catalysts have been used. However, these catalytic systems have a drawback that hydrocarbons having 6 and 7 carbon atoms cannot effectively be converted into the aromatic hydrocarbons.

Thus, in recent years, as a catalyst in which this drawback has been overcome, there has been found a catalyst in which platinum is supported on an L-type zeolite (Japanese Patent Publication No. 57408/1983). In this catalyst, a metal in the group VIII of the periodic table is supported on the L-type zeolite, but its activity is not sufficient and its life is inconveniently short. Afterward, for the sake of the improvement of the activity, a selectivity and the catalytic life and the simplification of a catalyst preparation method, various techniques have been suggested. For example, there have been suggested (1) a method which comprises supporting a metal in the group VIII on an L-type zeolite, and then subjecting it to an oxy-chlorination treatment to improve the catalytic activity and the life (Japanese Patent Application Laid-open No. 168539/1985), (2) a method which comprises treating an L-type zeolite with a solution containing a platinum salt and a non-platinum salt to improve platinum dispersion (Japanese Patent Application Laid-open No. 138539/1986), (3) a platinum catalyst supported on L-type zeolite treated with a halogen-containing compound (Japanese Patent Application Laid-open No. 57653/1987), (4) a platinum catalyst supported on L-type zeolite treated with a halogen-containing compound (Japanese Patent Application Laid-open No. 91334/1988), and (5) a simple catalyst preparation method which comprises the step of simultaneously supporting and treating a platinum component and one or more halogen components on an L-type zeolite (Japanese Patent Application Laid-open No. 49936/1993).

However, the above-mentioned method (1) has a drawback that a treating apparatus is complex, and the method (2) has a drawback that the catalytic activity is not sufficient. In addition, the catalysts of the above-mentioned (3) and (4) make use of Freon which is a harmful substance in a halogen treatment, and they have a drawback that a high-temperature treatment is carried out, so that dealumination takes place and hence a surface area decreases. Moreover, in the above-mentioned method (5), there is a drawback that the obtained catalyst has a high cracking activity.

As understood from the foregoing, each of the conventional catalysts in which platinum is supported on the L-type zeolite has the disadvantage, and for the reason, they have not been always sufficiently satisfactory.

SUMMARY OF THE INVENTION

The present invention has been developed under such circumstances, and an object of the present invention is to provide a platinum-supporting L-type zeolite catalyst which is desirable as a catalyst for the production of aromatic hydrocarbons and as a catalyst for the production of a gasoline having a high octane number and which can inhibit a cracking activity, can restrain the formation of coke (i.e., can restrain the deactivation of the catalyst by the coke), and can also improve an aromatic selectivity and a liquid yield.

Another object of the present invention is to provide a method for production of aromatic hydrocarbons and a gasoline having a high octane number by the use of this catalyst.

The present inventors have intensively researched to achieve the above-mentioned objects, and as a result, it has been found that a catalyst obtained by supporting a specific amount of at least one metal selected from the group Ib of the periodic table (hereinafter referred to as "the metal of the present invention" on occasion) on a conventional halogen and platinum supported on L-type zeolite is applicable to the achievement of the above-mentioned objects as a catalyst for the production of aromatic hydrocarbons and a gasoline having a high octane number. In addition, it has also been found that when a C6 fraction, a C7 fraction, a C8 fraction and fractions having the carbon number of more than eight ($C8^+$ fraction) or a mixed fraction thereof is brought into contact with the above-mentioned catalyst, aromatic hydrocarbons and a gasoline having a high octane number can efficiently be obtained. The present invention has been completed on the basis of these findings.

That is to say, (1) the first aspect of the present invention is directed to an L-type zeolite catalyst which is obtainable by supporting a platinum component, one or more halogen components and one or more metals components selected from the group Ib of the periodic table on an L-type zeolite, the support amount of the one or more metal components selected from the group Ib being in the range of 0.001 to 3% by weight based on the total weight of the catalyst in terms of the metal, a molar ratio of the one or more metal components selected from the group Ib/platinum being in the range of 0.01 to 1.

(2) The second aspect of the present invention is directed to a method for preparing the catalyst described in the above-mentioned paragraph (1) which comprises the steps of impregnating an L-type zeolite with a platinum-containing compound, one or more halogen-containing compounds and one or more metallic compounds selected from the group Ib of the periodic table, and then calcining the zeolite.

(3) The third aspect of the present invention is directed to a method for producing aromatic hydrocarbons which comprises the step of bringing at least one fraction selected from a C6 fraction, a C7 fraction, and a $C8^+$ fraction into contact with a catalyst described in the above-mentioned paragraph (1).

(4) The fourth aspect of the present invention is directed to a method for producing a gasoline having a high octane number which comprises the step of bringing one or more fractions selected from a C6 fraction, a C7 fraction, and a $C8^+$ fraction into contact with a catalyst described in the above-mentioned paragraph (1).

DETAILED DESCRIPTION OF THE INVENTION

An L-type zeolite catalyst of the present invention is a catalyst in which a platinum component, one or more halogen components and one or more metal components of the present invention are supported on an L-type zeolite, and this L-type zeolite can be represented by the composition formula $$0.9\text{–}1.3\mathrm{M}_{2/n}\mathrm{O}\cdot\mathrm{Al}_2\mathrm{O}_3\cdot 5.0\text{–}7.0\mathrm{SiO}_2\cdot 0\text{–}9\mathrm{H}_2\mathrm{O}$$

wherein M is an alkali metal or an alkaline earth metal; and n is a valence of M. Typically, there can be used the zeolites disclosed on pages 9 and 10 of Japanese Patent Application Laid-open No. 133835/1983 and on page 5 of Japanese Patent Application Laid-open No. 80333/1984.

Examples of the metal selected from the group Ib of the periodic table which can be used in the present invention include gold, silver and copper, and in the present invention, gold is preferable. In the L-type zeolite catalyst of the present invention, the support amount of the one or more metal components of the present invention are selected within the range of 0.001 to 3% by weight based on the total weight of the catalyst in terms of the metal. If the support amount of the metal component of the present invention deviates from this range, there cannot be obtained any catalyst having an excellent performance that a cracking activity and the formation of coke can be restrained and an aromatic selectivity and a liquid yield can also be improved, so that the objects of the present invention cannot be achieved. Furthermore, a molar ratio of the one or more metals of the present invention/platinum is in the range of 0.01 to 1, and if it deviates from this range, any catalyst having the above-mentioned performance cannot be obtained, so that the objects of the present invention cannot be achieved. In view of the catalytic performance, the molar ratio of the one or more metals of the present invention/platinum is preferably in the range of 0.03 to 0.5.

Furthermore, no particular restriction is put on the support amount of the platinum component, but in view of the catalytic performance, the support amount of the platinum component is preferably in the range of 0.1 to 5.0% by weight, more preferably 0.3 to 1.5% by weight, based on the total weight of the catalyst in terms of platinum. In addition, no particular restriction is put on the support amount of the one or more halogen components, but in view of the catalytic performance, the support amount of the one or more halogen components is preferably in the range of 0.1 to 5.0% by weight based on the total weight of the catalyst in terms of one or more halogens.

Moreover, in the L-type zeolite catalyst of the present invention, it is preferable that a dealumination amount in the L-type zeolite is small, and the dealumination amount is usually in the range of 0 to 3.0% by weight, preferably 0 to 2.0% by weight, more preferably 0 to 1.0% by weight based on an aluminum amount in the framework of the L-type zeolite.

Here, the dealumination amount in the L-type zeolite can be measured in accordance with the following procedure. A ratio of the coordination of an aluminum atom around an Si atom is obtained by the measurement of $^{29}$Si—NMR, and on the basis of the obtained ratio, an aluminum amount in the framework is calculated. The thus calculated aluminum amount is then compared to an aluminum amount in the framework of the raw material L-type zeolite measured in the same manner.

Subsequently, no particular restriction is put on a method for preparing the L-type zeolite catalyst of the present invention, and any method is acceptable, so long as it permits supporting the platinum component, the one or more halogen components and the one or more metal components of the present invention on the L-type zeolite. According to the following method of the present invention, the desired L-type zeolite catalyst can efficiently be prepared.

In the method of the present invention, the L-type zeolite is impregnated with the platinum-containing compound, the one or more halogen-containing compounds and the one or more metal-containing compounds of the present invention.

Prior to the molding of the L-type zeolite, a natural or a synthetic inorganic oxide such as alumina, silica or an aluminosilicate can be added to the L-type zeolite as a binder, if necessary. The amount of this binder to be added is preferably in the range of 5 to 90% by weight based on the total weight of the catalyst.

No particular restriction is put on the above-mentioned platinum-containing compound, and any compound is acceptable, so long as it becomes a platinum source, but a platinum salt is usually used. Examples of the platinum salt include tetrammineplatinum chloride, chloroplatinic acid, chloroplatinates, tetrammineplatinum hydroxide and dinitrodiaminoplatinum. These platinum-containing compounds may be used singly or in a combination of two or more thereof.

Furthermore, examples of the halogen-containing compound include various compounds. Typical examples thereof include chlorine-containing compounds such as hydrogen chloride and ammonium chloride, fluorine-containing compounds such as hydrogen fluoride and ammonium fluoride, iodine-containing compounds such as hydrogen iodide and ammonium iodide, and bromine-containing compounds such as hydrogen bromide and ammonium bromide. These halogen-containing compounds may be used singly or in a combination of two or more thereof.

In addition, no particular restriction is put on the metal-containing compound of the present invention, and any compound is acceptable, so long as it becomes a metal source. Usual examples thereof include gold chloride, chloroauric acid, sodium chloroaurate, silver nitrate, silver acetate, copper chloride, copper nitrate and copper acetate. These metallic compounds of the present invention may be used singly or in a combination of two or more thereof.

A method for the impregnation of the respective components is not particularly restricted, and the impregnation can be accomplished by any of an atmospheric pressure impregnation method, a vacuum impregnation method, an osmosis method and an ion exchange method which have usually been used. In this impregnation treatment, the L-type zeolite may be impregnated with the respective components simultaneously or successively. In the case of the successive impregnation, no particular restriction is put on the impregnation order of the respective components. Alternatively, two compounds and one compound may separately and successively be used for the impregnation. In the case of this successive impregnation, the L-type zeolite may be impregnated with another compound, after the serial operations of the impregnation, a drying treatment and a calcination treatment as needed.

After such an impregnation treatment, it is usual that the drying treatment is carried out, followed by the calcination treatment. The drying treatment may be done under atmospheric pressure or reduced pressure in a still state or a moving state, but a vacuum (reduced pressure) rotary drying method is preferably used. A drying temperature is suitably selected in the range of usually 40 to 200° C., preferably 70 to 150° C. Furthermore, the calcination treatment is carried out at a temperature higher than the drying treatment temperature, and it is usually done at a temperature in the range of 250 to 350° C. A calcination treatment atmosphere is not particularly restricted, but it is usually done in air. Air may be allowed to flow.

The thus obtained L-type zeolite catalyst of the present invention can suitably be used as a catalyst for the production of aromatic hydrocarbons or a gasoline having a high octane number.

In the L-type zeolite catalyst of the present invention, the one or more metals of the present invention are contained, whereby the metal of the present invention and platinum interact with each other to restrain the hydrogenolysis activity of platinum. In consequence, a gas selectivity decreases. In the case that the catalyst of the present invention is used as a catalyst for the production of aromatic hydrocarbons, these aromatic hydrocarbons can advantageously be obtained in a high yield by using, as a raw material, one or more fractions selected from a C6 fraction, a C7 fraction, and a C8$^+$ fraction, for example, each fraction of C6–C9, C7–C9, C8–C9, C6–C8, C7–C8, C7 and C8, or a fraction called a raffinate.

Alternatively, in the case that the catalyst of the present invention is used as a catalyst for the production of a gasoline having a high octane number from each fraction of C6–C9, C7–C9, C8–C9, C6–C8, C7–C8, C7 and C8, or a raffinate fraction, the gasoline can be produced in a high liquid yield, and there is also an advantage that a production ratio of benzene is low, which is a harmful substance and which is produced by the cyclizing dehydrogenation of C6 formed by the dealkylation of C7 and aromatic hydrocarbons having the carbon number of more than seven (C7$^+$ hydrocarbons) and the hydrogenolysis of C7$^+$ hydrocarbons.

Furthermore, there is also an advantage that the generation of coke which can be considered to be produced by the polymerization of a hydrocracked substance can be restrained, so that the deactivation of the catalyst by the coke can be inhibited.

The present invention intends to provide a method for preparing aromatic hydrocarbons and a method for producing a gasoline having a high octane number.

According to the method of the present invention, one or more fractions selected from the C6 fraction, the C7 fraction, and the C8$^+$ fraction is brought into contact with the L-type zeolite catalyst of the present invention to thereby obtain the aromatic hydrocarbons or the gasoline.

Examples of the C6 fraction, the C7 fraction, and the C8$^+$ fraction include paraffin hydrocarbons, olefin hydrocarbons, acetylene hydrocarbons, cyclic paraffin hydrocarbons and cyclic olefin hydrocarbons.

The above-mentioned paraffin hydrocarbons preferably have 6 to 10 carbon atoms, and typical examples thereof include n-hexane, methylpentane, n-heptane, methylhexane, dimethylpentane, n-octane, methylheptane and dimethylhexane.

Moreover, the above-mentioned olefin hydrocarbons preferably have 6 to 10 carbon atoms, and typical examples thereof include hexene, methylpentene, heptene, methylhexene, dimethylpentene and octene. In addition, the above-mentioned acetylene hydrocarbons preferably have 6 to 10 carbon atoms, and typical examples thereof include hexine, heptine and octine.

The above-mentioned cyclic paraffin hydrocarbons preferably have 6 to 10 carbon atoms, and typical examples thereof include methylcyclopentane, cyclohexane, methylcyclohexane and dimethylcyclohexane.

Furthermore, the above-mentioned cyclic olefin hydrocarbons preferably have 6 to 10 carbon atoms, and typical examples thereof include methylcyclopentene, cyclohexene, methylcyclohexene and dimethylcyclohexene.

These hydrocarbons may be used singly or in a combination of two or more thereof. In addition, the raffinate can preferably be used.

No particular restriction is put on conditions in bringing the above-mentioned hydrocarbon into contact with the catalyst of the present invention, but in order to obtain successful results, it is advantageous that temperature is in the range of 350 to 600° C., preferably 400 to 550° C., pressure is in the range of 0 to 4 kg/cm$^2$G, preferably 0 to 10 kg/cm$^2$G, and liquid hour space velocity (LHSV) is in the range of 0.1 to 20 hr$^{-1}$, preferably 1 to 10 hr$^{-1}$. Moreover, a feed ratio of a hydrogen gas/a raw material hydrocarbon is preferably selected within the range of 0.1 to 50 mol/mol.

And then, the present invention will be described in more detail in accordance with examples, but the scope of the present invention should not be limited at all by these examples. It is to be noted that every catalyst obtained in the following examples contains 1% by weight of platinum.

EXAMPLE 1

20 parts by weight of a silica binder (trade name Snowtex, made by Nissan Chemical Co., Ltd.) was added to 100 parts by weight of an L-type zeolite (trade name TSZ-500KOA, made by Toso Co., Ltd.), followed by kneading and molding. Afterward, the thus molded sample was calcined at 500° C. for 2 hours in air to obtain a molded L-type zeolite with silica binder.

On the other hand, 0.086 g of tetrammineplatinum chloride, 0.088 g of ammonium fluoride, 0.019 g of ammonium chloride and 2.1 g of ion-exchanged water were mixed with each other to prepare a platinum e halogen-containing impregnation solution.

The thus prepared impregnation solution was slowly added dropwise to 5 g of the molded L-type zeolite with silica binder with stirring to impregnate the zeolite with the platinum-containing compound and the halogen-containing compound, and the impregnated zeolite was then heated from room temperature to 100° C. over 40 minutes, followed by a vacuum rotary drying treatment at 100° C. for 3 hours.

Subsequently, 0.4 g of a previously prepared aqueous sodium chloroaurate solution (containing 2.5% by weight of gold) was mixed with 1.7 g of ion-exchanged water to prepare a gold-containing impregnation solution, and the above-mentioned dried platinum e halogen-impregnated L-type zeolite was then impregnated with the gold-containing solution. Afterward, the thus treated zeolite was heated up to 100° C. over 40 minutes, under the vacuum rotary and kept at 100° C. for 3 hours, and then calcined at 320° C. for 1 hour in air to obtain a catalyst.

The amount of supported gold in this catalyst was 0.2% by weight, and a molar ratio of Au/Pt was 0.2.

COMPARATIVE EXAMPLE 1

In accordance with the same procedure as in Example 1, an L-type zeolite was impregnated with a platinum-containing compound and one or more halogen-containing compounds, dried, and, without any impregnation with a gold-containing compound, then calcined at 320° C. for 1 hour in air to obtain a catalyst.

EXAMPLE 2

The same procedure as in Example 1 was conducted except that a mixture of 0.1 g of a previously prepared aqueous sodium chloroaurate solution (containing 2.5% by weight of gold) and 2.0 g of ion-exchanged water was used as a gold-containing impregnation solution, thereby obtaining a catalyst.

The amount of supported gold in this catalyst was 0.05% by weight, and a molar ratio of Au/Pt was 0.05.

EXAMPLE 3

The same procedure as in Example 1 was conducted except that a mixture of 0.2 g of a previously prepared aqueous sodium chloroaurate solution (containing 2.5% by weight of gold) and 1.9 g of ion-exchanged water was used as a gold-containing impregnation solution, thereby obtaining a catalyst.

The amount of supported gold in this catalyst was 0.1% by weight, and a molar ratio of Au/Pt was 0.1.

EXAMPLE 4

The same procedure as in Example 1 was conducted except that a mixture of 0.6 g of a previously prepared aqueous sodium chloroaurate solution (containing 2.5% by weight of gold) and 1.5 g of ion-exchanged water was used as a gold-containing impregnation solution, thereby obtaining a catalyst.

The amount of supported gold in this catalyst was 0.3% by weight, and a molar ratio of Au/Pt was 0.3.

EXAMPLE 5

The same procedure as in Example 1 was conducted except that a mixture of 0.4 g of a previously prepared aqueous chloroauric acid solution (containing 2.5% by weight of gold) and 1.7 g of ion-exchanged water was used as a gold-containing impregnation solution, thereby obtaining a catalyst.

The amount of supported gold in this catalyst was 0.2% by weight, and a molar ratio of Au/Pt was 0.2.

EXAMPLE 6

By the use of catalysts obtained in Examples 1 to 5 and Comparative Example 1, the aromatization of n-octane was carried out.

50 mg of each catalyst was ground into 32 to 65 mesh and then filled into a reactor, and this reactor was set on a device. Afterward, it was heated from room temperature to 540° C. over 35 minutes at a hydrogen flow rate of 100 cc/min and then subjected to hydrogen reduction at 540° C. for 1 hour.

After the completion of the hydrogen reduction, a reaction temperature was adjusted to 470° C., and 1 microliter, 2 microliters and 3 microliters of n-octane were pulsed in a hydrogen gas flow (100 cc/min) to carry out a conversion reaction into aromatic hydrocarbons. An n-octane (n-C8) conversion, a C1–C4 gas yield and a C8 aromatic hydrocarbon (C8A) yield were obtained as follows. The results are shown in Table 1.

The n-C8 conversion (%)=[(weight of n-C8 at outlet)/(weight of n-C8 at inlet)]×100

The C1–C4 gas yield (wt %)=[(weight of C1–C4 at outlet)/(weight of n-C8 at inlet)]×100

The C8A yield (wt %)=[(weight of xylene+ethylbenzene at outlet)/(weight of n-C8 at inlet)]×100

TABLE 1

| Kind of Catalyst | | | C8A | C1–C4 Gas Yield |
|---|---|---|---|---|
| | Molar Ratio of Au/Pt | Gold-Containing Starting Material | Yield at 60% n-C8 Conversion (wt %) | at 60% n-C8 Conversion (wt %) |
| Example 1 | 0.2 | Sodium chloroaurate | 30.0 | 4.3 |
| Comparative Example 1 | 0 | — | 27.0 | 5.8 |
| Example 2 | 0.05 | Sodium chloroaurate | 30.0 | 4.5 |
| Example 3 | 0.1 | Sodium chloroaurate | 28.0 | 4.7 |
| Example 4 | 0.3 | Sodium chloroaurate | 30.5 | 5.2 |
| Example 5 | 0.2 | Chloroauric acid | 30.1 | 4.9 |

As is apparent from Table 1, an unnecessary C1–C4 gas content can be decreased at the same conversion and the C8A yield can be heightened by adding gold.

EXAMPLE 7

By the use of catalysts obtained in Examples 1 to 5 and Comparative Example 1, the aromatization of a C6 fraction was carried out.

50 mg of each catalyst was ground into 32 to 65 mesh and then filled into a reactor, and this reactor was set on a device. Afterward, it was heated from room temperature to 540° C. over 35 minutes at a hydrogen flow rate of 100 cc/min and then subjected to hydrogen reduction at 540° C. for 1 hour.

After the completion of the hydrogen reduction, a reaction temperature was adjusted to 470° C., and 2 microliters of the C6 fraction having a composition shown in Table 2 were pulsed in a hydrogen gas flow (100 cc/min) to carry out a conversion reaction into aromatic hydrocarbons. A benzene selectivity and a C1–C5 selectivity were obtained as follows. The results are shown in Table 3.

The benzene selectivity (wt %)=[(weight of benzene at outlet)/(weight of benzene+C1–C5 at outlet)]×100

The C1–C5 selectivity (wt %)=[(weight of C1–C5 at outlet)/(weight of benzene+C1–C5 at outlet)]×100

TABLE 2

| Substance | Composition (wt %) |
|---|---|
| 2,3-dimethylbutane | 0.7 |
| 2-methylpentane | 9.3 |
| 3-methylpentane | 15.3 |
| n-hexane | 59.7 |
| methylcyclopentane | 13.5 |
| 2,4-dimethylpentane | 1.0 |
| 3,3-dimethylpentane | 0.5 |

TABLE 3

| | Gold Content (wt %) | Gold-Containing Starting Material | Benzene Selectivity (wt %) | C1–C5 Selectivity (wt %) |
|---|---|---|---|---|
| | Kind of Catalyst | | | |
| Example 1 | 0.2 | Sodium chloroaurate | 94.4 | 5.6 |
| Comparative Example 1 | 0 | — | 90.5 | 9.5 |
| Example 2 | 0.05 | Sodium chloroaurate | 95.0 | 5.0 |
| Example 3 | 0.1 | Sodium chloroaurate | 94.3 | 5.7 |
| Example 4 | 0.3 | Sodium chloroaurate | 92.4 | 7.6 |
| Example 5 | 0.2 | Chloroauric acid | 94.0 | 6.0 |

As is apparent from Table 3, the selectivity of C1–C5 which are the cracked products decreases by adding gold, so that the selectivity of benzene which is the desired product can be improved.

EXAMPLE 8

By the use of catalysts obtained in Example 1 and Comparative Example 1, a raffinate as a raw material was subjected to a conversion reaction.

The raffinate as the raw material having a composition shown in Table 4 was allowed to react under a reaction pressure of 4 kg/cm²G in the presence of 0.5 g of the catalyst in a hydrogen/raffinate molar ratio of 3 at a weight hour space velocity (WHSV) of 2 hr$^{-1}$ by the use of a fixed bed flow type reactor. In this case, a reaction temperature was regulated so that a research octane number (RON) of a C5$^+$ fraction might be 103. Here, the RON was a value in the case that n-hexane, benzene, methylcyclopentane and isoheptane were omitted.

The results of yields regarding the resultant products are shown in Table 5.

TABLE 4

| | Paraffin | Naphthene | Aromatic | Total |
|---|---|---|---|---|
| | Raffinate Composition (wt %) | | | |
| C5 | 0.4 | 0.1 | — | 0.5 |
| C6 | 12.0 | 4.3 | 0.7 | 17.0 |
| C7 | 34.6 | 9.6 | 4.8 | 49.0 |
| C8 | 13.8 | 5.2 | 4.4 | 23.4 |
| C9 | 7.2 | 1.8 | 0.7 | 9.7 |
| C10$^+$ | 0.2 | 0.1 | 0.1 | 0.4 |
| Total | 68.2 | 21.1 | 10.7 | 100.0 |

TABLE 5

| | | Example 1 (containing 0.2 wt % of gold) | Comparative Example 2 (not containing any gold) |
|---|---|---|---|
| | | Kind of Catalyst | |
| Yield (wt %) | H$_2$ | 4.2 | 4.2 |
| | C1–C4 | 4.8 | 6.3 |
| | C5$^+$ | 91.0 | 89.5 |
| | Aromatic | | |
| | Benzene | 12.5 | 16.4 |
| | Toluene | 37.1 | 36.7 |
| | C8 Aromatic | 15.0 | 13.5 |

Table 5 indicates that when the catalyst of Example 1 is used, a yield of the C5$^+$ fraction is higher, a cracking selectivity is lower. These facts mean that the catalyst of Example 1 is more excellent in terms of liquid yield. In addition, it is apparent that the production of benzene, which is suspected to be a carcinogen and whose concentration in a gasoline is restricted, is restrained.

Furthermore, as a catalyst for the production of aromatic hydrocarbons, the catalyst of Example 8 has an advantage that it can provide, in a high yield, a C8 aromatic hydrocarbon which is useful as a petrochemical raw material.

EXAMPLE 9

A molded L-type zeolite with silica binder obtained in Example 1 was ground into 20 to 40 mesh, vacuum-dried at 110° C. for 4 hours, and then further calcined at 200° C. for 2 hours and at 500° C. for 2 hours in a muffle furnace.

And then, 0.0046 g of gold chloride (AuCl$_3$) was dissolved in such an amount of ion-exchanged water as to be just absorbed by 5 g of this carrier, thereby preparing a gold-containing impregnation solution. Subsequently, 5 g of the ground carrier was impregnated with this impregnation solution. Afterward, it was vacuum-dried at 110° C. for 4 hours, and then calcined at 300° C. for 2 hours in the muffle furnace.

And then, 0.089 g of tetrammineplatinum chloride, 0.088 g of ammonium fluoride and 0.039 g of ammonium chloride were dissolved in such an amount of ion-exchanged water as to be absorbed by the above-mentioned gold-supporting sample, thereby preparing a platinum • halogen-containing impregnation solution. Then, 5 g of the gold-supporting sample was impregnated with this impregnation solution, allowed to stand at room temperature overnight, and then vacuum-dried at 110° C. for 3 hours. Afterward, the impregnated sample was calcined at 150° C. for 30 minutes, at 250° C. for 30 minutes, and at 300° C. for 1 hour.

The amount of supported gold in this catalyst was 0.06% by weight, and a molar ratio of Au/Pt was 0.06.

EXAMPLE 10

The same procedure as in Example 9 was conducted except that the amount of gold chloride was 0.0091 g and that of ammonium chloride was 0.036 g, thereby preparing a catalyst.

The amount of supported gold in this catalyst was 0.12% by weight, and a molar ratio of Au/Pt was 0.12.

EXAMPLE 11

The same procedure as in Example 9 was conducted except that the amount of gold chloride was 0.019 g and that of ammonium chloride was 0.031 g, thereby preparing a catalyst.

The amount of supported gold in this catalyst was 0.25% by weight, and a molar ratio of Au/Pt was 0.25.

EXAMPLE 12

The same procedure as in Example 9 was conducted except that 0.0046 g of gold chloride was replaced with 0.0035 g of silver nitrate and the amount of ammonium chloride was 0.041 g, thereby preparing a catalyst.

The amount of supported silver in this catalyst was 0.044% by weight, and a molar ratio of Ag/Pt was 0.08.

EXAMPLE 13

The same procedure as in Example 9 was conducted except that 0.0046 g of gold chloride was replaced with 0.0035 g of copper nitrate and the amount of ammonium chloride was 0.041 g, thereby preparing a catalyst.

The amount of supported copper in this catalyst was 0.02% by weight, and a molar ratio of Cu/Pt was 0.06.

EXAMPLE 14

By the use of catalysts obtained in Examples 9 to 13 and Comparative Example 1, the aromatization of a raffinate was carried out.

A raffinate raw material having the composition shown in Table 6 was mixed with hydrogen and passed over 1.0 gram of catalyst in a fixed bed flow type reactor, at a pressure of 3.4 kg/cm$^2$G. The weight hourly space velocity of the raw material was 4.4 hr$^{-1}$ and the hydrogen to hydrocarbon molar ratio was 5. Initially, the reaction temperature was set at 468° C. in order to determine the relative activity. The temperature was then adjusted to achieve about 80 wt % conversion of C6$^+$ non-aromatics. The fouling rate was then determined by letting the activity decline at constant reaction temperature. The relative activity, deactivation rate, C6$^+$ non-aromatic conversion, selectivity to aromatics+hydrogen, and C8 aromatics selectivity were obtained by the following procedures. The results are shown in Table 7.

(1) The relative activity=constant×ln[1/(1−X)]

X=[(weight of C6$^+$ non-aromatics in raw material)−(weight of C6$^+$ non-aromatics at outlet)]/(weight of C6$^+$ non-aromatics in raw material)

The constant was decided so that the relative activity of the catalyst in Comparative Example 1 might be 1.

(2) The relative fouling rate=a ratio of a decline velocity of the relative activity in the case that the fouling rate of the catalyst in Comparative Example 1 is regarded as 1.

(3) The C6$^+$ non-aromatic conversion (wt %)=[{(weight of C6$^+$ non-aromatic hydrocarbons in raw material)−(weight of C6$^+$ non-aromatic hydrocarbons at outlet)}/(weight of C6$^+$ non-aromatic hydrocarbons in raw material)]×100

(4) The aromatic+H$_2$ selectivity (wt %)=[{(weight of aromatic+H$_2$ at outlet)−(weight of aromatic hydrocarbons in raw material)}/{(weight of C6$^+$ non-aromatic hydrocarbons in the raw material)−(weight of C6$^+$ non-aromatics at outlet)}]×100

(5) The C8 aromatic selectivity (wt %)=[{(weight of C8 aromatic hydrocarbons at outlet)}−(weight of C8 aromatic hydrocarbons in raw material)}/{(weight of C8 non-aromatic hydrocarbons in raw material)−(weight of C8 non-aromatic hydrocarbons at outlet)}]×100

TABLE 6

| | Raffinate Composition (volume %) | | | |
|---|---|---|---|---|
| | Paraffin | Naphthene | Aromatic | Total |
| C5 | 0.6 | 1.5 | — | 2.1 |
| C6 | 37.3 | 5.6 | 0.1 | 43.0 |
| C7 | 36.2 | 2.0 | 0.7 | 38.9 |
| C8 | 10.0 | 2.3 | 2.2 | 14.5 |
| C9 | 0.8 | 0.5 | 0.2 | 1.5 |
| Total | 84.9 | 11.9 | 3.2 | 100.0 |

TABLE 7

| Kind of Catalyst | | | | C8 Aromatic Selectivity |
|---|---|---|---|---|
| | Atomic Ratio of Group 1b Metal to Platinum | Relative Activity | Relative Fouling Rate | at C6$^+$ Non-aromatic Conversion of 80% (wt %) |
| Comparative Example 1 | 0 | 1 | 1 | 64 |
| Example 9 | 0.06 (Au) | 0.7 | 0.2 | 68 |
| Example 10 | 0.12 (Au) | 0.7 | 0.4 | 69 |
| Example 11 | 0.25 (Au) | 0.9 | 0.4 | 72 |
| Example 12 | 0.08 (Ag) | 0.6 | 0.9 | 65 |
| Example 13 | 0.06 (Cu) | 0.6 | 0.5 | 69 |

As understood from Table 7, when gold, silver or copper is added, the C8 aromatic selectivities can be improved, though the relative activities are slightly deteriorated. In addition, the relative fouling rate can remarkably be lowered, whereby the stability of the catalysts can sufficiently be increased.

The gold-containing catalyst of the present invention can inhibit a cracking activity, can restrain the formation of coke (i.e., can restrain the deactivation of the catalyst by the coke), and can also improve an aromatic selectivity and a liquid yield, and hence, it is desirable as a catalyst for the production of aromatic hydrocarbons and a gasoline having a high octane number.

What is claimed is:

1. An L-type zeolite catalyst which is obtainable by supporting a platinum component, one or more halogen components and one or more metal components selected from the group Ib of the periodic table on an L-type zeolite, the support amount of the one or more metal components selected from the group Ib being in the range of 0.001 to 3% by weight based on the total weight of the catalyst in terms of the metal, a molar ratio of the one or more metal components selected from the group Ib/platinum being in the range of 0.01 to 1.

2. The catalyst according to claim 1 wherein the metal selected from the group Ib of the periodic table is gold.

3. The catalyst of claim 2, wherein the amount of supported platinum is in the range of 0.1 to 5.0% by weight based on the total weight of the catalyst.

4. The catalyst of claim 2, wherein the amount of the supported one or more halogens is in the range of 0.1 to 5.0% by weight based on the total weight of the catalyst.

5. The catalyst of claim 2, wherein the amount of supported platinum is in the range of 0.1 to 5.0% by weight based on the total weight of the catalyst and the amount of the supported one or more halogens is in the range of 0.1 to 5.0% by weight based on the total weight of the catalyst.

6. The catalyst according to claim 1 wherein the amount of supported platinum is in the range of 0.1 to 5.0% by weight based on the total weight of the catalyst.

7. The catalyst according to claim 1 wherein the amount of the supported one or more halogens is in the range of 0.1 to 5.0% by weight based on the total weight of the catalyst.

8. A method for preparing the catalyst of claim 1 which comprises the steps of impregnating an L-type zeolite with a platinum-containing compound, a halogen-containing compound and one or more metallic compounds selected from the group Ib of the periodic table, and then calcining the zeolite.

9. The catalyst of claim 1, wherein the amount of supported platinum is in the range of 0.1 to 5.0% by weight based on the total weight of the catalyst and the amount of the supported one or more halogens is in the range of 0.1 to 5.0% by weight based on the total weight of the catalyst.

10. A method for producing aromatic hydrocarbons which comprises the step of bringing one or more fractions selected from a C6 fraction, a C7 fraction, and a $C8^+$ fraction into contact with the catalyst of claim 1.

11. A method for producing a gasoline having a high octane number which comprises the step of bringing one or more fractions selected from a C6 fraction, a C7 fraction, and a $C8^+$ fraction into contact with the catalyst of claim 1.

12. A method for producing aromatic hydrocarbons which comprises the step of bringing one or more fractions selected from a C6 fraction, a C7 fraction and a $C8^+$ fraction into contact with the catalyst of claim 2.

13. A method for producing a gasoline having a high octane number which comprises the step of bringing one or more fractions selected from a C6 fraction, a C7 fraction and a $C8^+$ fraction into contact with the catalyst of claim 2.

* * * * *